(12) United States Patent
Aerts et al.

(10) Patent No.: US 9,303,525 B2
(45) Date of Patent: Apr. 5, 2016

(54) METHOD AND ARRANGEMENT FOR MULTI-CAMERA CALIBRATION

(75) Inventors: Maarten Aerts, Beveren-Waas (BE); Donny Tytgat, Ghent (BE); Jean-Francois Macq, Ganshoren (BE); Sammy Lievens, Brasschaat (BE)

(73) Assignee: Alcatel Lucent, Boulogne-Billancourt (FR)

( * ) Notice: Subject to any disclaimer, the term of this patent is extended or adjusted under 35 U.S.C. 154(b) by 790 days.

(21) Appl. No.: 13/582,164

(22) PCT Filed: Mar. 8, 2011

(86) PCT No.: PCT/EP2011/053483
§ 371 (c)(1),
(2), (4) Date: Nov. 27, 2012

(87) PCT Pub. No.: WO2011/117069
PCT Pub. Date: Sep. 29, 2011

(65) Prior Publication Data
US 2013/0070108 A1 Mar. 21, 2013

(30) Foreign Application Priority Data

Mar. 26, 2010 (EP) .................................... 10305309

(51) Int. Cl.
*F01D 21/00* (2006.01)
*G06T 7/00* (2006.01)
(Continued)

(52) U.S. Cl.
CPC .............. *F01D 21/003* (2013.01); *F01D 25/00* (2013.01); *G01N 21/15* (2013.01); *G01N 21/85* (2013.01);
(Continued)

(58) Field of Classification Search
CPC ....... G06T 7/002; F01D 21/003; F01D 25/00; G01N 21/85; G01N 21/15; G02B 23/2492
See application file for complete search history.

(56) References Cited

U.S. PATENT DOCUMENTS 7,313,265 B2 * 12/2007 Nakai et al. .................... 382/154
7,512,261 B2 * 3/2009 Lou et al. ....................... 382/154
(Continued)

FOREIGN PATENT DOCUMENTS

CN 101127128 2/2008
JP 2004334819 11/2004
(Continued)

OTHER PUBLICATIONS

Cornelis, K. et al.; Online Calibration of Two Zoom-Pan-Tilt Units for Planar Dynamic Events; dagm 2006; vol. LNCS 4174; pp. 698-707; 2006; Springer-Verlag Berlin Heidelberg 2006.
(Continued)

*Primary Examiner* — Jefferey Harold
*Assistant Examiner* — Sean Haiem
(74) *Attorney, Agent, or Firm* — Patti & Malvone Law Group, LLC (57) ABSTRACT

A method for determining calibration data for at least two cameras (camera1, camera2) in a multi view position, includes a step of determining respective parameters $((h^1_{00}, \ldots, h^1_{22}), (h^2_{00}, \ldots, h^2_{22}))$ for identifying at least one respective homographic transformation on respective images (image1, image2) taken by said cameras of a same scene, by performing respective geometry analyses on said respective images (image1, image2), a step of performing at least one respective combined homographic transformation/feature detection step on said respective images thereby obtaining respective sets (feature set1, feature set2) of features on respective transformed images, such that said calibration data are obtained from matches $(m_1, \ldots, m_k)$ determined between said respective sets of features.

20 Claims, 9 Drawing Sheets (51) Int. Cl.
　　　*F01D 25/00*　　　(2006.01)
　　　*G01N 21/15*　　　(2006.01)
　　　*G01N 21/85*　　　(2006.01)
　　　*G02B 23/24*　　　(2006.01)
　　　*G01N 21/954*　　(2006.01)

(52) U.S. Cl.
　　　CPC ............ *G02B 23/2492* (2013.01); *G06T 7/002* (2013.01); *F05D 2260/80* (2013.01); *G01N 21/954* (2013.01); *G01N 2021/151* (2013.01); *G01N 2201/08* (2013.01); *G06T 2207/10012* (2013.01)

(56) References Cited

U.S. PATENT DOCUMENTS

| | | | | |
|---|---|---|---|---|
| 8,917,317 | B1* | 12/2014 | Beeler | 348/47 |
| 2002/0158873 | A1* | 10/2002 | Williamson | 345/427 |
| 2003/0202691 | A1* | 10/2003 | Beardsley | 382/154 |
| 2004/0085451 | A1* | 5/2004 | Chang | 348/159 |
| 2005/0237385 | A1* | 10/2005 | Kosaka et al. | 348/42 |
| 2009/0153669 | A1 | 6/2009 | Kim et al. | |
| 2012/0007943 | A1* | 1/2012 | Tytgat | 348/14.08 |

FOREIGN PATENT DOCUMENTS

| | | |
|---|---|---|
| JP | 2006042361 | 2/2006 |
| WO | 2008049404 | 5/2008 |

OTHER PUBLICATIONS

Roman Pflugfelder et al; People Tracking across two distant self-calibrated cameras; IEEE Conference on Advanced Video and Signal Based Surveillance, Sep. 5, 2007; pp. 393-398; XP55028172; retrieved from the internet URL:http://ieeexplore.ieee.org/ielx5/4425265/4425266/04425343.pdf?tp=&arnumber=4425343&isnumber=4425266; retrieved on May 25, 2012.

Roman Pflugfelder et al; Self-Calibrating cameras in Video Surveillance; Dissertation; May 1, 2008; XP55028170; Retrieved from the internet: URL:http://www.icg.tugraz.at/publications/pdf/pflugfelder2008a; retrieved on May 25, 2012.

Sung Chun Lee et al; Automatic Pose Estimation of Complex 3D Building Models; Applications of Computer Vision; 2002; (WACV 2002); Proceedings, Sixth IEEE Workshop on Dec. 3-4, 2002; Piscataway, NJ; USA; IEEE; Dec. 3, 2002; pp. 148-152; XP010628740; ISBN: 978-0-7695-1858-9.

Julien Pilet et al; An All-In-One Solution to Geometric and Photometric Calibration; Mixed and Augmented Reality, 2006, ISMAR 2006; IEEE/ACM International Symposium On, IEEE, PI; Oct. 1, 2006; pp. 69-78; XP031014652; ISBN: 978-1-4244-0650-0.

\* cited by examiner

METHOD AND ARRANGEMENT FOR MULTI-CAMERA CALIBRATION

The present invention relates to a method for determining calibration data between a plurality of cameras.

BACKGROUND

Calibration data of multiple cameras from different viewpoints are used whenever data from one camera has to be related to data from another camera e.g. during a full 3D reconstruction of a scene viewed by these cameras, when performing 3D tracking of people or during applications of computer generated graphics as for instance used in augmented reality applications.

Calibration data generally comprises intrinsic and extrinsic camera parameters. The former relate to metrics of the internal camera itself, such as pixel size, aspect ratio, skew and principal point. The extrinsic calibration data relate to the camera's position and viewing direction, either relative to a specified world frame, or to another (reference) camera.

The internal calibration parameters do not depend on the position of the camera, and can therefore be assumed to be known, as these are generally either given by the camera vendor or be estimated.

On the other hand, the relative position as well as the viewing directions of the cameras are unknown variables. They change each time a camera is displaced, or moved, e.g. during the creation of movie images, or during image capturing using a mobile device, or during movement of webcams capturing the images.

Known techniques for providing these extrinsic calibration data usually involve some human intervention, where either these positions are manually measured, or obtained by means of some manual intervention techniques. Fully automatic techniques exist, but only for limited cases of differences in position and viewing angle between the cameras, since it is difficult to deal with deformations in images resulting from different viewpoints. These limited cases only refer to e.g. short distances between the cameras as well as small angle viewpoint differences.

It is thus an object of embodiments of the present invention to provide a method of the above known kind, but which is fully automatic, and can work for multiple cameras irrespective of their relative position.

SUMMARY

According to embodiments of the invention this object is achieved by the method including a step of determining respective parameters for identifying at least one respective homographic transformation on respective images taken by said cameras of a same scene, by performing respective geometry analyses on said respective images, a step of performing at least one respective combined homographic transformation/feature detection step on said respective images thereby obtaining respective sets of features on respective transformed images, such that said calibration data are obtained from matches determined between said respective sets of features.

In this way a universal and fully automated technique is obtained by determining the parameters which identify at least one proper homographic transformation on the respective images, captured by the cameras of a same scene. These homographic transformations are itself dependent of the camera and scene setup and are determined by performing a geometry analysis of the respective images. Furthermore, by determining corresponding items or matches between respective sets of features on the respective transformed images, external calibration parameters from one camera relative to the other, can be obtained.

This procedure can be repeated as needed with any pair of cameras in the whole set to achieve a calibration of the full multitude of cameras.

The calibration data may thus comprise information with respect to the relative position and/or the relative viewing direction differences between the cameras. The relative position can be expressed by means of the relative distance whereas the relative viewing direction differences can be expressed by means of the relative tilting, rolling and panning angle differences between the cameras.

The parameters identifying the respective homographic transformations can be determined by geometry analysis of the captured scene, thus of the respective images. This can be done in a multitude of relatively simple ways as will become clear from the embodiments described in further parts of this document. One variant may involve using detected line segments in the respective images of the cameras, whereas another may e.g. involve the comparison of curved segments on these images. Also analysis of line angles, perpendicularity and parallelism may be exploited, as may more higher level techniques as detecting rectangles and even object recognition. In yet other variants combinations of these techniques can be used.

Depending on the type of scene geometry analysis used, one or more homographic transformations can be computed per image.

Further features are further described in the appended claims and in the description.

The present invention relates as well to device for performing embodiments of the present method, to a computer program adapted to perform any of the embodiments of the method and to a computer readable storage medium comprising such a computer program.

It is to be noticed that the term 'comprising', used in the claims, should not be interpreted as being limitative to the means listed thereafter. Thus, the scope of the expression 'a device comprising means A and B' should not be limited to devices consisting only of components A and B. It means that with respect to the present invention, the only relevant components of the device are A and B.

BRIEF DESCRIPTION OF DRAWINGS

The above and other objects and features of the invention will become more apparent and the invention itself will be best understood by referring to the following description of an embodiment taken in conjunction with the accompanying drawings wherein.

DETAILED DESCRIPTION

The description and drawings merely illustrate the principles of the invention. It will thus be appreciated that those skilled in the art will be able to devise various arrangements that, although not explicitly described or shown herein, embody the principles of the invention and are included within its spirit and scope. Furthermore, all examples recited herein are principally intended expressly to be only for pedagogical purposes to aid the reader in understanding the principles of the invention and the concepts contributed by the inventor(s) to furthering the art, and are to be construed as being without limitation to such specifically recited examples and conditions. Moreover, all statements herein reciting principles, aspects, and embodiments of the invention, as well as specific examples thereof, are intended to encompass equivalents thereof.

It should be appreciated by those skilled in the art that any block diagrams herein represent conceptual views of illustrative circuitry embodying the principles of the invention. Similarly, it will be appreciated that any flow charts, flow diagrams, state transition diagrams, pseudo code, and the like represent various processes which may be substantially represented in computer readable medium and so executed by a computer or processor, whether or not such computer or processor is explicitly shown.

The functions of the various elements shown in the figures, may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, network processor, application specific integrated circuit (ASIC), field programmable gate array (FPGA), read only memory (ROM) for storing software, random access memory (RAM), and non volatile storage. Other hardware, conventional and/or custom, may also be included. Similarly, any switches shown in the FIGS. are conceptual only. Their function may be carried out through the operation of program logic, through dedicated logic, through the interaction of program control and dedicated logic, or even manually, the particular technique being selectable by the implementer as more specifically understood from the context.

Figure 1A:
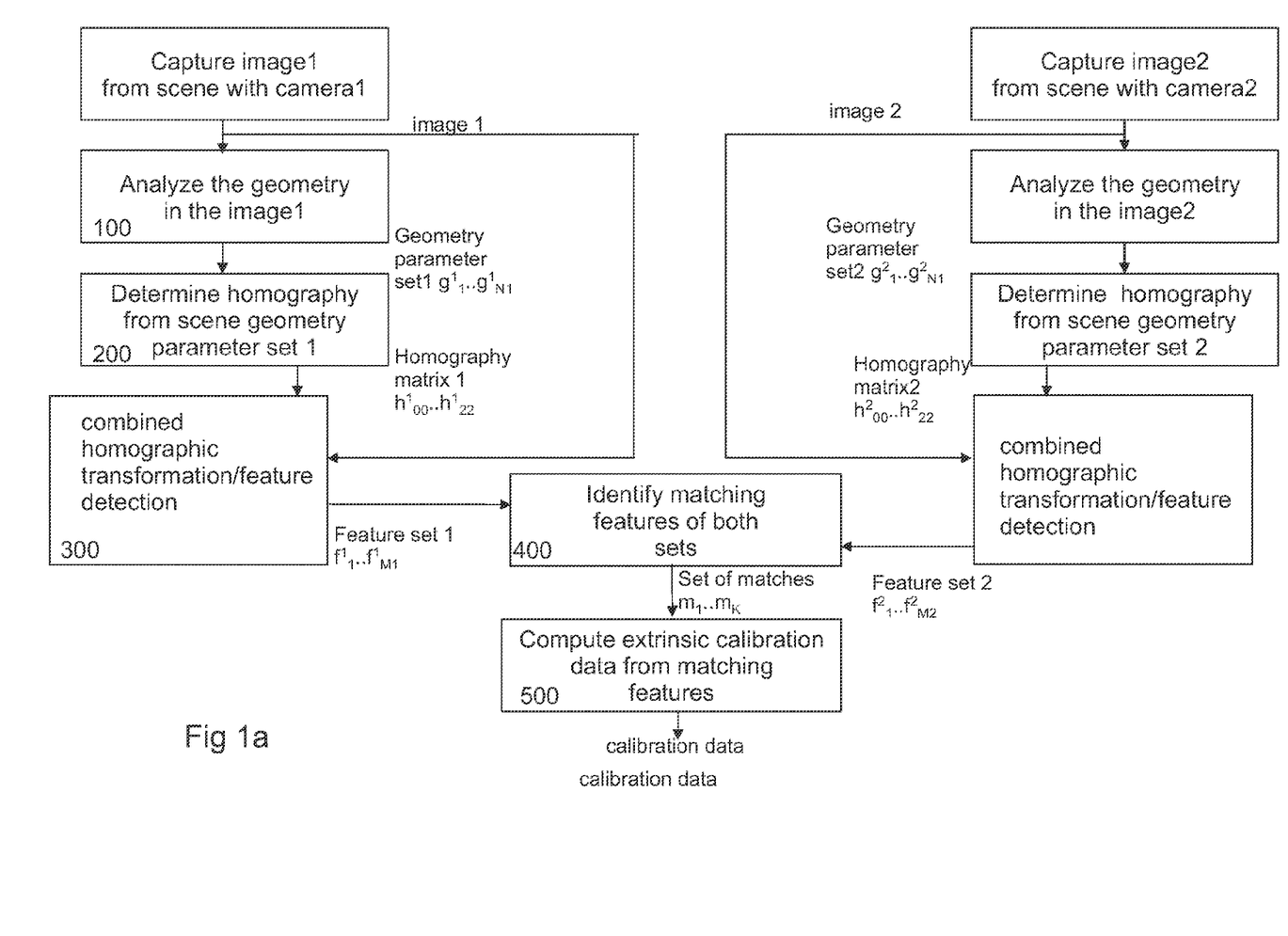
FIG. 1a shows a high-level schematic block scheme of an embodiment of the method.
Figure 2A:
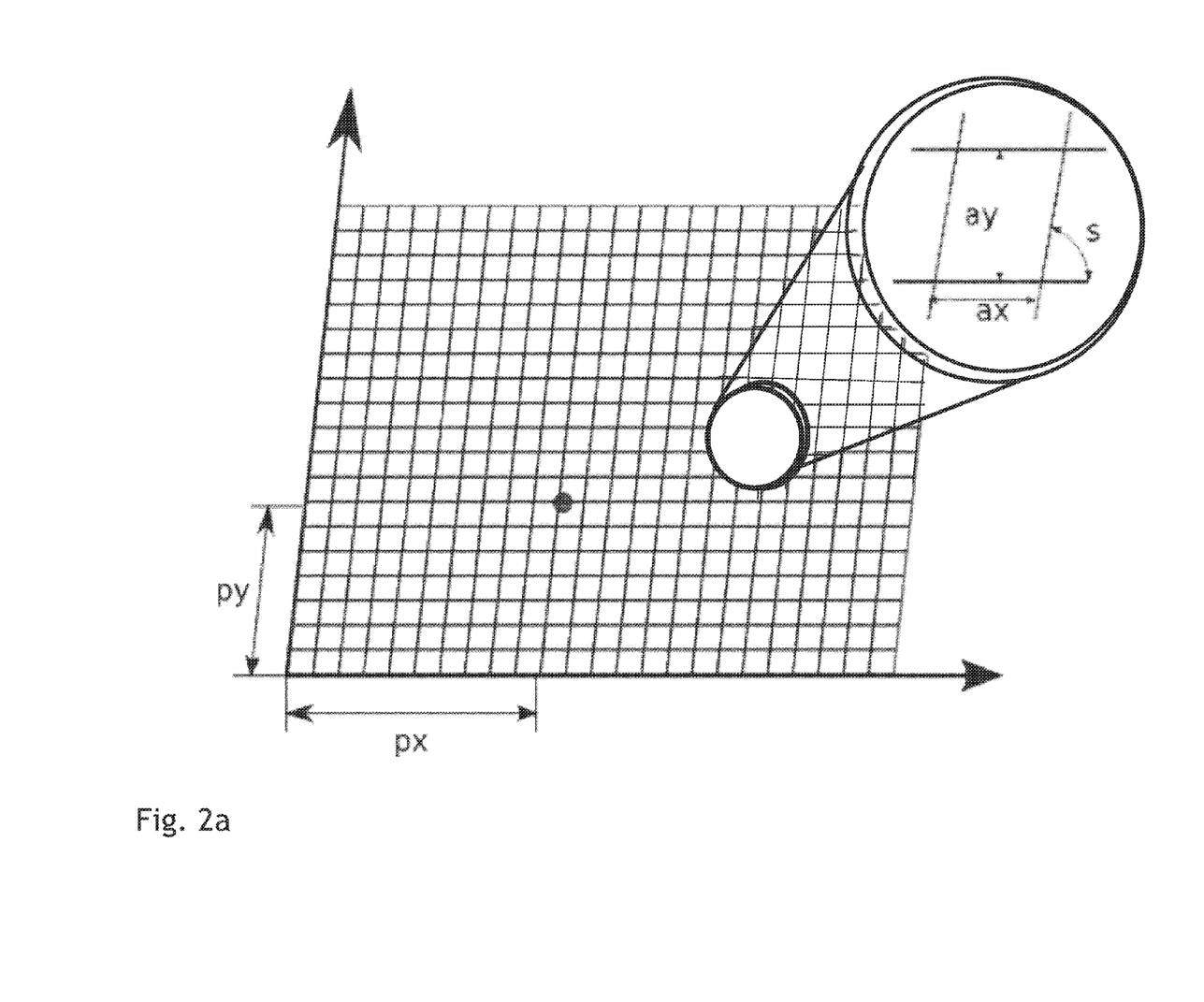

FIG. 1a shows a high level embodiment of the method for determining calibration data for two cameras. It is evident that this embodiment is as well applicable to a multiple camera situation with more than 2 cameras as well. The calibration data generally comprise intrinsic and extrinsic camera parameters. These are respectively shown in FIGS. 2a and 2b. The intrinsic camera parameters relate to the metrics of the internal of the camera itself, such as shown in FIG. 2a, e.g. related to the two components of the principal point px and py as well as the pixel width (ax), height (ay) and skew (s).

Figure 2B:
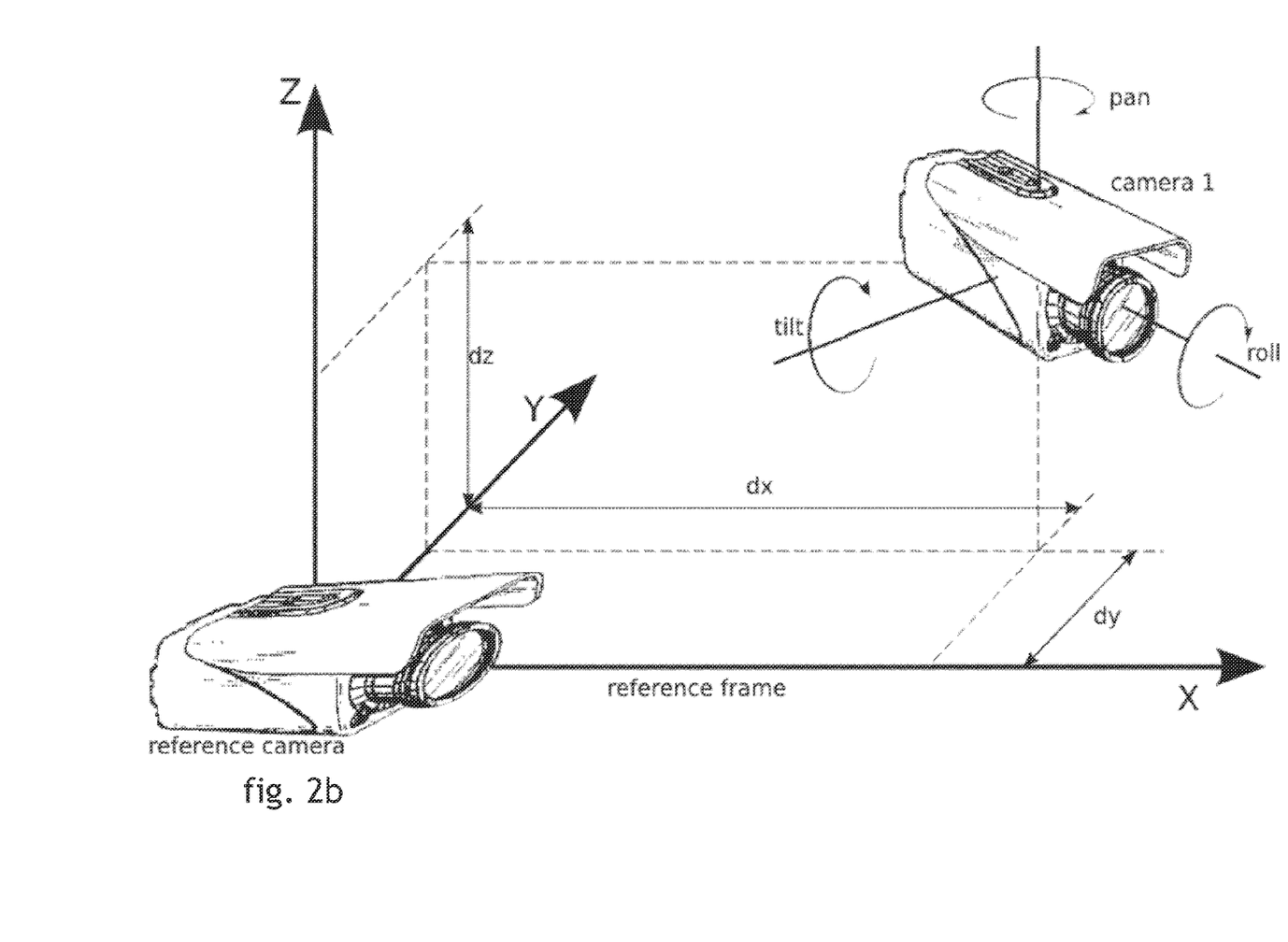

FIG. 2b shows the extrinsic camera parameters, related to the relative position between these cameras and their viewing direction. In general one of the cameras will be taken as a reference camera, and the relative position and relative viewing direction of the other ones are then determined with respect to this reference camera, for all individual cameras of the set. The relative position is denoted as (dx,dy,dz), referring to the three components of the position vector of camera 1 with respect to the reference camera. The panning, tilting and rolling angle comprise the three components of the difference in viewing direction of camera 1, with respect to the reference viewing direction of the reference camera.

The cameras of which the calibration data are to be determined are positioned in a multi-view position, meaning that they are all capable of taking a picture more or less from the same scene. With scene is meant any object, scenery, human being, animation, etc. which can be optically registered by a camera. Thus a "scene" is not only limited to ordinary pictures of human beings, landscapes etc, but also to virtual or real objects whichever are detectable by a camera.

Contrary to prior an methods, embodiments of the present methods will be able to generate extrinsic camera calibration data, irrespective of the relative distance and difference in orientation between these cameras.

These extrinsic camera parameters thus relate to a difference in distance, e.g. the difference between the two focal points of the cameras or the focal point of one camera and the reference frame's origin. In general this difference can be expressed as a position vector comprising these 3 different distance components as depicted in FIG. 2b. The difference in the 3 rotation angles, being the tilt, pan and roll angles as shown on FIG. 2b and well known by a person skilled in the art, is generally expressed by means of a rotation matrix R, which can be computed from these three angles $\alpha, \beta, \gamma$ $$R = \begin{bmatrix} \cos\gamma & \sin\gamma & 0 \\ -\sin\gamma & \cos\gamma & 0 \\ 0 & 0 & 1 \end{bmatrix} \begin{bmatrix} 1 & 0 & 0 \\ 0 & \cos\beta & \sin\beta \\ 0 & -\sin\beta & \cos\beta \end{bmatrix} \begin{bmatrix} \cos\alpha & \sin\alpha & 0 \\ -\sin\alpha & \cos\alpha & 0 \\ 0 & 0 & 1 \end{bmatrix} \quad (1)$$

In order to obtain these calibration data between the different cameras, respective images are taken from a same scene or object by means of the respective cameras. In the embodiment of FIG. 1a these pictures are denoted image 1, respectively image 2. These images are used for determining the parameters which define at least one homographic transformation which is subsequently to be performed on these images or on parts thereof. To this end, the scene's geometry is analyzed. This step is denoted 100 for the geometry analysis of image 1 as shown in FIG. 1a.

There exist various ways to perform this geometry analysis and some are explained in further embodiments. In contrast to other methods, which may exhaustively try out all types of homographic transformations on the images, the geometry analysis step used in embodiments of this invention will enable to quickly identify one or more appropriate homographic transformations. This will result in a reduction of computation time for determining the calibration parameters and an increase of the ratio of the number of correct feature matches to the total number of feature matches, used by this latter step, and thus its usability and accuracy.

A homographic transformation can involve rectifying horizontal planes, mimicking a bird's eye's view or rectifying vertical planes to create a front or side view, . . . . Such a homographic transformation is determined by a transformation matrix H $$H = \begin{bmatrix} h_{00} & h_{01} & h_{02} \\ h_{10} & h_{11} & h_{12} \\ h_{20} & h_{21} & h_{22} \end{bmatrix} \quad (2)$$

to be performed on each pixel (x, y) of the images. Each of the transformed pixel coordinates (x', y') can then be expressed by means of homogeneous coordinates ($x'_h$, $y'_h$, $t'_h$) with $t'_h$ representing a ratio factor such that for each pixel following transformation is to be performed;

$$\begin{bmatrix} x'_h \\ y'_h \\ t'_h \end{bmatrix} = \begin{bmatrix} h_{00} & h_{01} & h_{02} \\ h_{10} & h_{11} & h_{12} \\ h_{20} & h_{21} & h_{22} \end{bmatrix} \begin{bmatrix} x \\ y \\ 1 \end{bmatrix} \text{ and } x' = \frac{x'_h}{t'_h}, y' = \frac{y'_h}{t'_h} \quad (3)$$

Referring back to FIG. 1a, the respective homographic transformation determination for image 1 is denoted as step 200. A next step involves a combined homographic transformation/feature detection to be applied to the respective images from which the scene geometry parameters were derived such as to enable the generation of the transformation parameters.

Figure 1B:
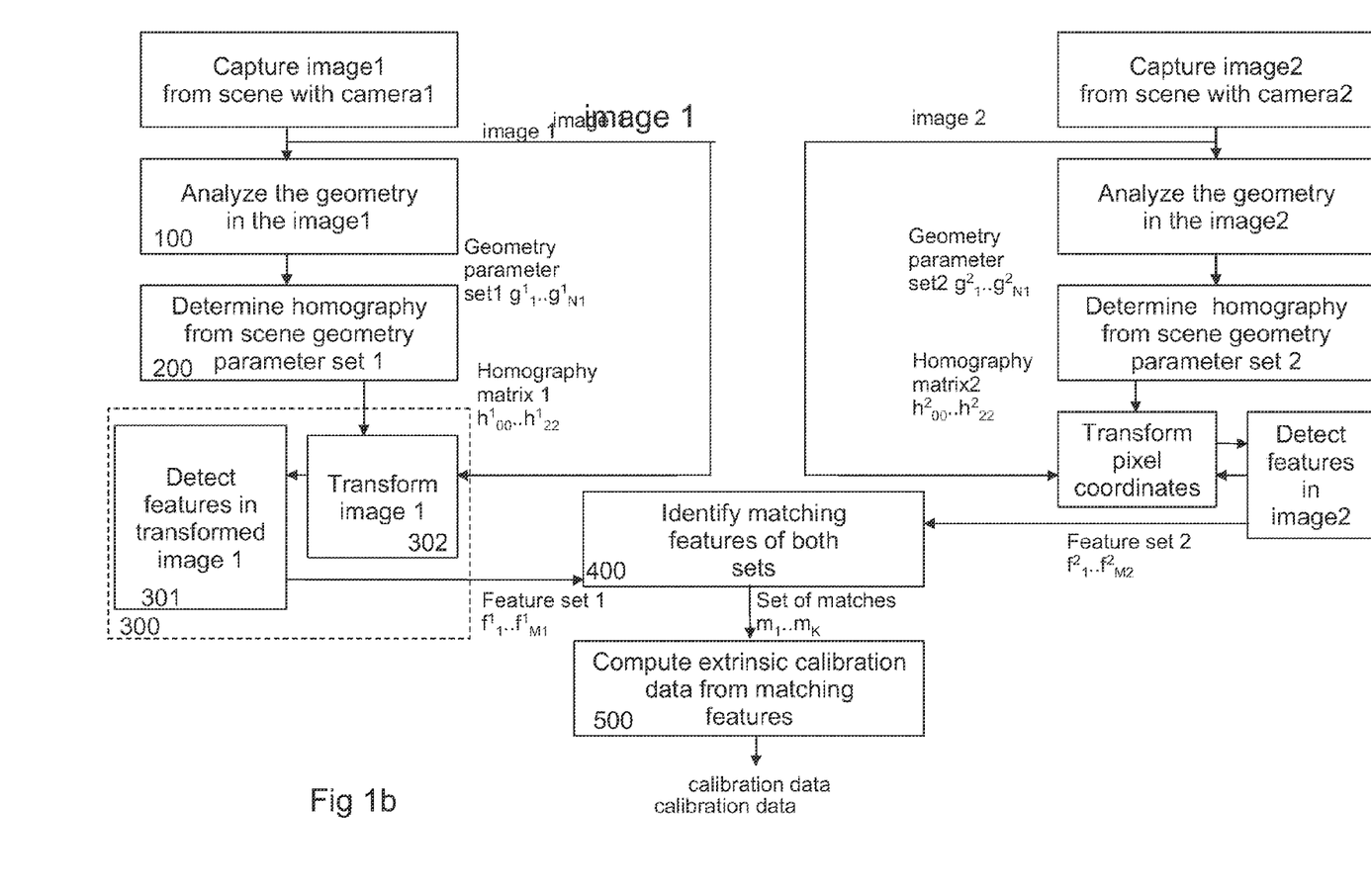
FIG. 1b shows a first variant embodiment of the high level block scheme of FIG. 1a, FIG. 1c shows a second variant embodiment of the high level block scheme of FIG. 1a, FIG. 2a schematically shows the intrinsic calibration parameters of a camera, FIG. 2b schematically shows the extrinsic calibration parameters of a camera.
Figure 1C:
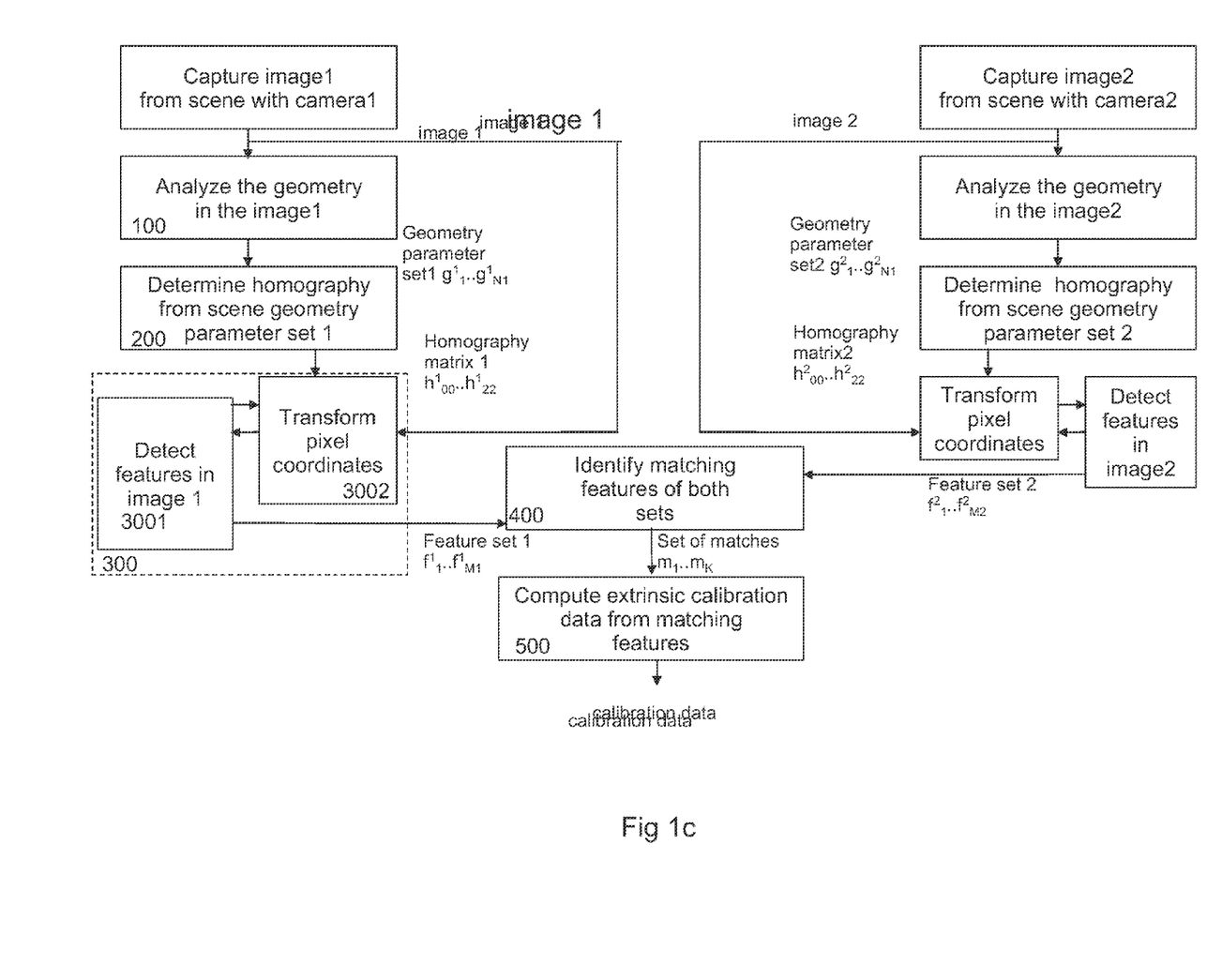

This combined transformation/feature detection step, denoted 300 for image 1 on FIG. 1a, may comprise a complete transformation 302 of the complete image after which step feature detection 301 will be performed on the transformed images as shown in FIG. 1b. In yet other embodiments, such as the one shown in FIG. 1c, the feature detection step 3001 is adapted in such a way that each time the detector accesses a pixel in the image the pixel coordinates are first transformed by the homographic transformation 3002, before the pixel information in the original image is fetched. For all these embodiments the result of combined transformation/feature detection step 300 will be a respective set of features on transformed images, denoted feature set 1 for image 1 and feature set 2 for image 2 on FIGS. 1a,b and c.

Feature detection can be performed based on similarity invariant feature detection methods. Several different algorithms exist to this purpose such as detecting edges, corners, blobs or regions using methods as SIFT which is the abbreviation of Scale Invariant Feature Transform, SURF which is the abbreviation of Speeded Up Robust Features, GLOH being the abbreviation of Gradient Location and Orientation Histogram, Harris, MSER being the abbreviation of Maximaly Stable Extremal Regions, Tomasi, block matching, . . . etc. Since these algorithms are all prone to perform badly under deformation other than similarity involving mere scaling, translation and rotation, they cannot be applied directly on the input images, hence the need for performing homographic transformations first.

Once the features are detected on the transformed images, matches are to be searched for. Matched features may include corresponding pixels, corresponding lines, corresponding objects, corresponding regions etc. If the type of scene geometry extracted in the first stage permits features are matched between corresponding transformed images, resulting from both cameras. If not, all features resulting from all homographic transformations of one camera are compared against all features resulting from the second camera. Therefore in some embodiments such as the one depicted in FIG. 3a-b, several of these homographic transformations are determined on the respective images, as it may be the case that one geometry analysis may result in several appropriate homographies. This is then again followed by a combined transformation/feature detection step of the respective images for all determined transformations, such as to obtain again a set of transformed features, where this set will then comprise all transformed features for all homographic transformations. Matched items are then again to be found between the sets of transformed features for both images.

The set of matched items or attributes for both transformed images is denoted m1 to mk in FIGS. 1a-c, and FIGS. 3a-b, referring to k pairs of matched attributes between the two transformed images. These matched items can then be used for determining the calibration data, such as the earlier mentioned rotation matrix and position vector.

Again depending on the type of scene geometry of the first step, the matching step and the extraction of the calibration data may be aided by the scene parameters or the homographic transformations themselves as will be explained into more detailed embodiments.

Corresponding features of the transformed images are thus used to derive the extrinsic calibration parameters between the two cameras. Since the features subside in the transformed images, their respective homographic transformations are taken into account when using these features to extract the calibration data. Depending on the type of scene geometry parameters, these parameters may also further help to refine the subspace of possible calibration solutions, although this is not required. Using epipolar geometry or other back-projecting techniques, the relative position vector and rotation matrix can be computed from the correspondences.

Figure 3A:
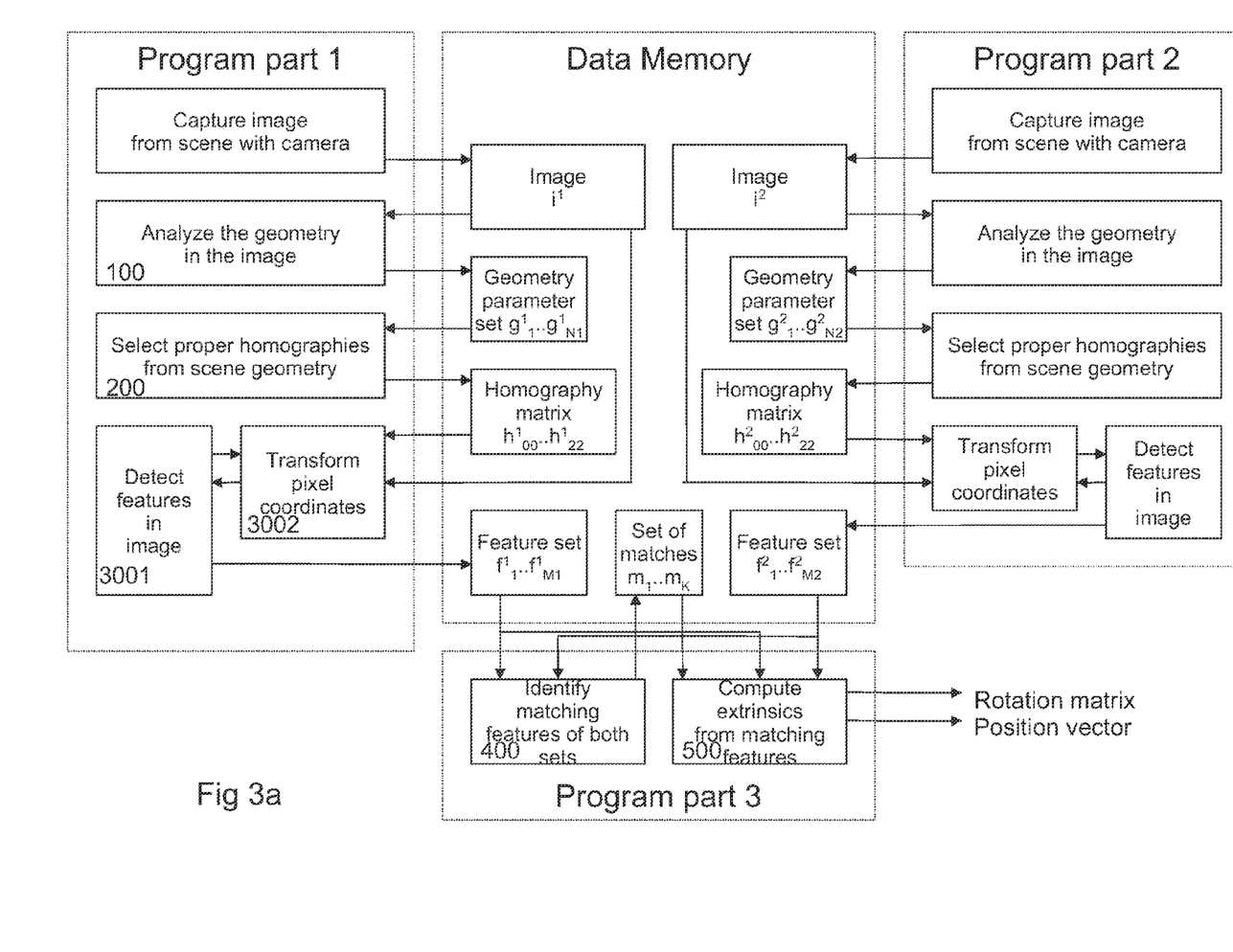
FIG. 3a shows a computer implementation of the first variant embodiment depicted in FIG. 1c.
Figure 3B:
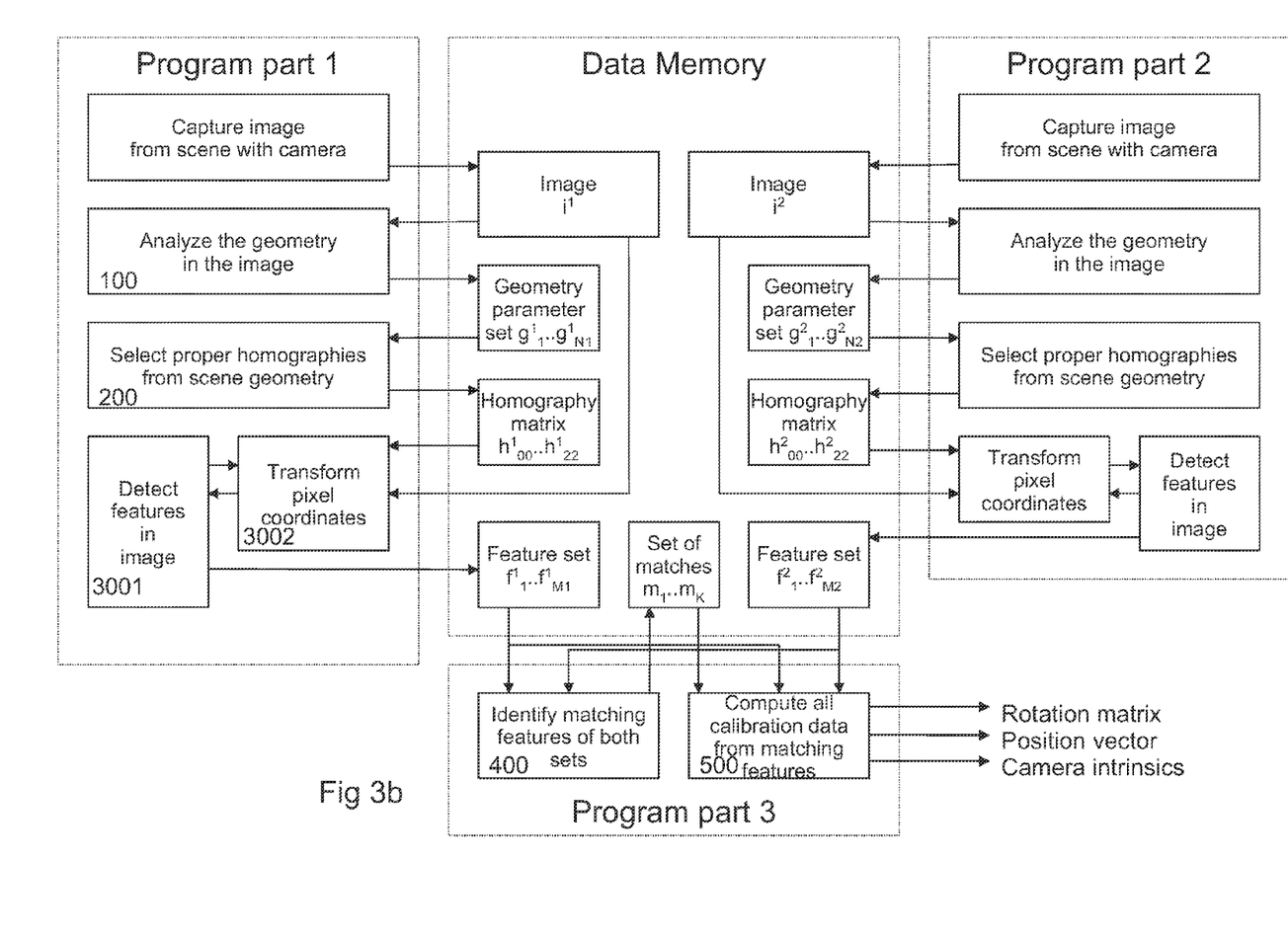
FIG. 3b shows a variant of the implementation of FIG. 3a, where also intrinsic calibration parameters are calculated.

FIGS. 3a and 3b depict respective computer implementations of the described methods. The variant depicted in FIG. 3a is based upon the variant method of FIG. 1c and further comprises a selection of several homographies in step 200. Furthermore, during the calculation of the extrinsic calibration parameters not only the set of matches are taken into account, but also the features themselves. This may be interesting for these embodiments where the matches themselves do not comprise information related to the position of the features within the original images themselves, as this position is used for the determination of the calibration data. In the embodiments with reference to FIGS. 1a-c, it is assumed that the matches do contain this information.

The variant depicted in FIG. 3b is similar to the one of FIG. 3a, but in step 500 not only extrinsic but also intrinsic calibration data are further calculated.

A more detailed computer-realizable embodiment now be described, including a more detailed explanation of the geometry analysis and feature detection and matching steps and with reference to FIGS. 4a-b. This embodiment is preferably used for man-made scenes, thus for calibrating cameras capturing non-natural, often also denoted as man-made scenes, such as indoor scenes, urban scenes, typically featuring parallel lines, aligned objects etc. This embodiment will exploit the abundance of vertical and to a lesser extent horizontal lines in the scene, to find a common vertical vanishing point.

Each camera which is to be calibrated will again take a picture of the scene. As the steps to be performed are similar for both cameras, only the steps with reference to the first camera are shown in FIGS. 4a and b.

Figure 4A:
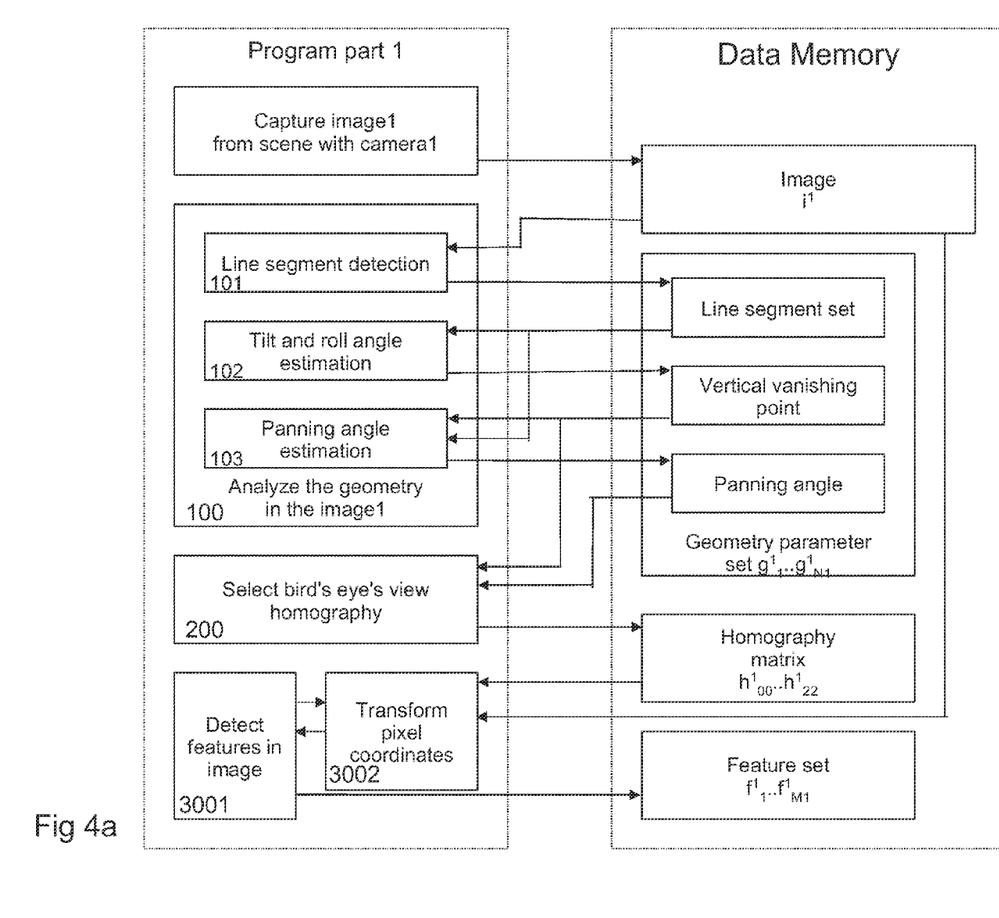
FIGS. 4a-b show more detailed embodiments of the embodiment of FIG. 3a which can preferably be used for non-natural scenes.

The geometry analysis 100 on the image taken by camera 1, in FIG. 4a denoted image i1, involves performing a line segment detection step 101 as the image from a man-made scene generally contains a lot of these lines. Methods for doing this may comprise Hough Transforms, LSD, curvature analysis, SLIDE, combinatorial optimization methods, clustering, . . . . In another variant the method may also comprise an initial filtering step.

Once the line segments are detected, they can be used to perform a tilt and roll angle estimation in step 102. This may involve a search for a vertical vanishing point.

Based on the tilt and roll angle estimation, a panning angle estimation is performed in step 103.

Once all these angles including the panning angle are estimated, the geometry parameter set denoted $g^1_1 \ldots g'_{N1}$ is complete. The homographic transformation parameters can then be determined based on this set. In this case they will be based upon a bird's eye's view homography.

Such a bird's eye view homographic transformation corresponds to rectifications and the detailed computation of the parameters will be explained in a later paragraph.

The thus calculated parameters $(h^1_{00}, \ldots, h^1_{22})$ can then be used for performing these rectifications on the different images. The thus obtained rectified images respectively will then undergo a search for matching or corresponding features. Again this can be done in various way.

As previously explained the features may be detected on the transformed images, after which step the matches are determined from the respective feature sets. An implementation based on a scale invariant feature detection method will again be explained with reference to FIG. 4b.

Figure 4B:
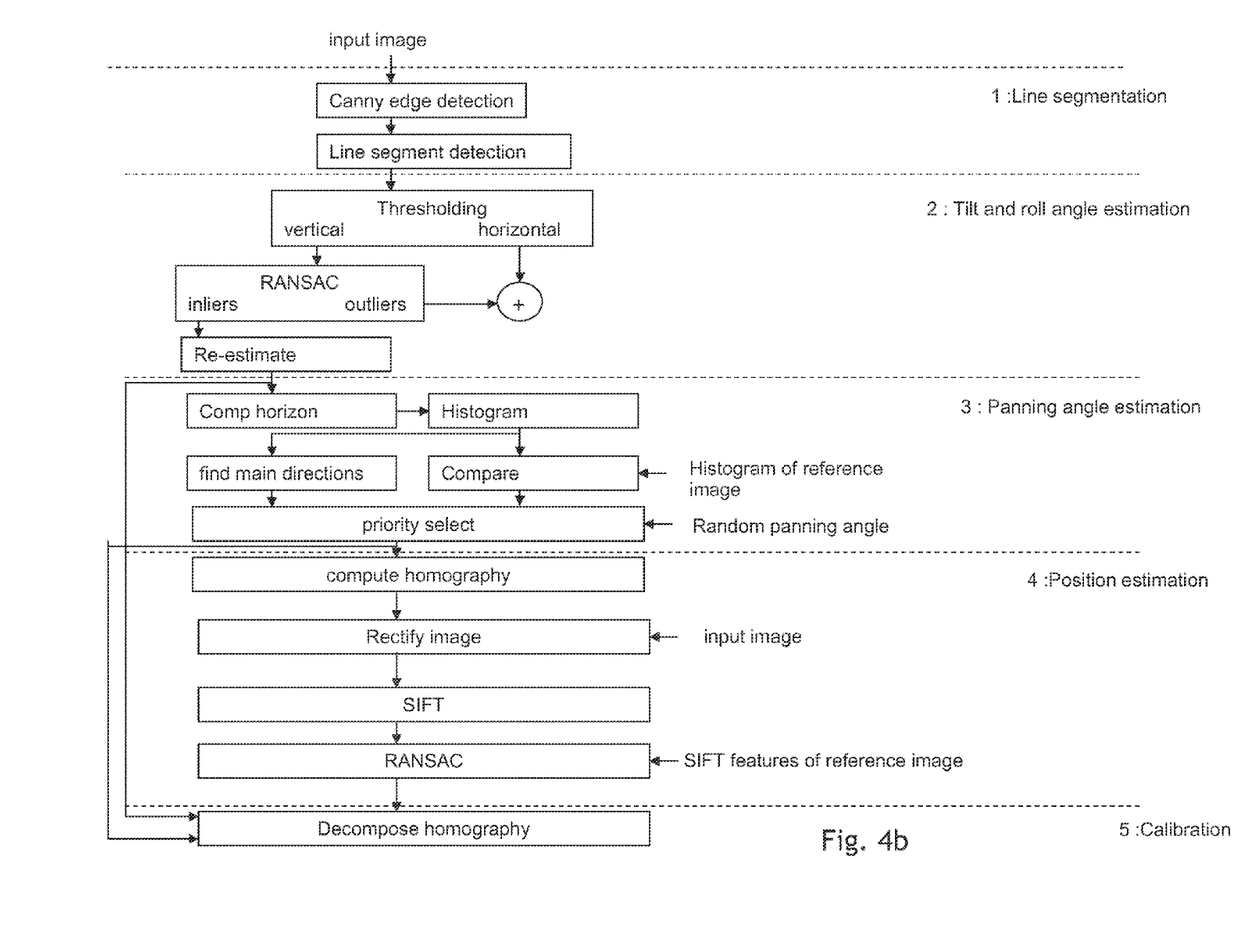

This FIG. 4b further gives some further detailed embodiments for each of the different steps outlined in FIG. 4a.

With respect to stage 101 of FIG. 4a, related to line segment detection, the embodiment depicted in FIG. 4b includes an initial filtering step on each of the images. In this embodiment of FIG. 4b this is realized by means of an edge detection filter. The images of each camera in the network are thereby filtered to binary images showing all edges in the images. Although there are different possibilities for performing this initial filtering step, a preferred solution makes use of the Canny Edge Detector, because it's robust in many applications and does not require many parameter settings. Because the algorithm runs along the edges in an image, a fast integrated implementation with the next steps is possible. Alternatives may include using simple gradient methods like Sobel filters, Laplacian filters, Difference-of-Gaussian filters, . . . .

This edge detection filtering is followed by a step for detecting line segments in the binary edge output generated by the filtering operation. Again line segment detection can be done in various ways. A preferred embodiment allowing a fast integration with the previous filtering step involves evaluating the curvature of the edge while running along it in the edge detection step. At edge pixels where the accumulated curvature is high, the edge is cut and a new possible line segment is formed. Short line segments are discarded. Line segments representing the same line are merged.

Once the line segments are then detected, a tilt and roll angle estimation stage 102 is to be performed on them. This can be done by means of searching for the vertical vanishing point, which in itself may comprise three steps. A vanishing point is a point where the projections of lines, which are parallel in real world, seem to intersect in an image. A first step roughly classifies the line segments into likely vertical ones and ones likely to lie in a horizontal plane. Since for this particular embodiment it is assumed that the camera has no large roll angle (= rotation around optical axis, see FIG. 2b), it can also be assumed that the projection of vertical lines in the scene is more or less vertical. Therefore all lines with angles differing less than e.g. 20 degrees from vertical are separated from the other ones, being denoted "horizontal" in FIG. 4b, by a thresholding operation with these e.g. 20 degrees deviation from vertical being the threshold value. Note that other, less simplified embodiments don't require assumptions like this.

RANSAC, being the abbreviation of Random Sample Consensus, being a robust variant for selecting good candidates for vertical vanishing points and eliminating false ones, is next applied to the selected vertical lines. This may be performed in an iterative way where during each iteration two likely vertical lines from the previous stage are selected. The intersection of these two lines will then be proposed as a vertical vanishing point candidate. If many other likely vertical lines pass this point at a distance below some limit value, this point candidate gets a higher score. This iteration is then repeated many times. The vanishing point candidate with the highest score and corresponding vertical lines, denoted "inliers" are passed through to a final refinement step, being denoted "re-estimate". Remaining lines, denoted "outliers" are added to the list of horizontally classified lines from the previously performed thresholding step.

This "re-estimating" step refines the optimal vanishing point from all selected vertical lines below the threshold, rather than computing the intersection of just two lines as in the previous step. At this point, the camera's orientations with respect to the vertical direction being the tilt angle and around the optical axis, being the roll angle are known, since from Eq. 1 follows that these two angles are only dependent on one column of the rotation matrix, which is exactly defined by the normalized homogeneous coordinates of this vanishing point.

It is to be remarked that at this point any horizontal plane can be rectified by a homographic transformation in a way to reduce deformations to the similarity class (i.e. merely translation, rotation and scaling) between two views of different cameras. Therefore it is possible to skip the panning angle estimation step 103 and go straight to the transformation step. However, in order to ease and to improve the accuracy of this loiter step, in this embodiment a panning angle estimation is present.

The panning angle is the angle around the vertical axis (see FIG. 2b). Its determination may involve three sub-steps. In a first sub-step, the horizon of each view is computed. This horizon corresponds to the line where all projections of horizontal planes intersect in an image. All vanishing points of any direction in a horizontal plane will be on this line. There exists even a one-to-one relation between the points on this line and the horizontal direction angles. This line can be computed from the vertical vanishing point and the camera's aforementioned intrinsic calibration parameters shown in FIG. 2a. More specific, points on this line form the same subspace as the mathematical null-space of the normalized vanishing point. If the internal calibration is not known, an estimate is good enough for the purpose of this stage, since the technique will be robust to slight changes of the horizon. An estimate can easily be derived solely from the image width and height, which are of course known.

Once the horizon is obtained, each non-vertical line being the union of horizontally thresholded lines and the ones discarded by RANSAC, will be intersected with this horizon to derive its horizontal direction. Since measures of lines, estimates of horizons and finding intersections are highly subject to noise, a histogram of line directions for each image will be generated. Each line is hereby weighted by its length.

A second sub-step involves searching for 'main directions' in these histograms, which allows a direct calibration relative to the scene. Maxima in the histogram correspond to horizontal line directions which are abundant in the scene. This occurs often in man-made scenes, because people tend to find aligned objects more esthetical than unordered ones. Moreover, these maxima and their corresponding main directions are often 90 degrees apart, which can be exploited by the maximum-finding algorithm, resulting in two main directions per view, so the panning angle is defined up to a n*90 degree ambiguity. This ambiguity can be resolved by performing the steps in stage 4 (homographic transformation and SIFT) 4 times, for panning angles phi, phi+90, phi+180 and phi+270. This doesn't mean a four times doubled time complexity thouah, since most steps in the next stage can do the 4 angles at once.

However, it may happen that no main directions appear from the histograms. In this case one can always fall back on finding the difference in panning angle between the camera and a reference camera, rather than relating the histogram to a common reference frame. The histograms for each image are compared with respect to each other in order to derive the relative panning angle between the two cameras which had generated the pair of images currently compared. To this purpose the smoothed histogram of one view has to be shifted by a sampled subset of the panning angle search space until it minimizes some distance criterion with the other smoothed histogram. One could use Kullback-Leibe divergence as the criterion and a simple Parzen windowing for smoothing. Other choices are available of course.

If the 'main-directions' path and the 'panning angle difference' path both fail, the priority select step will select random panning angles for both images and leave resolving this ambiguity up to the matching step of stage 4 of FIG. 4b. At this point, the cameras' full orientations with respect to each other, and possibly—if main directions could be found—with rasped to the main directions in the scene, are found by means of the determination of the tilt, roll and pan angles. Next steps will deal with finding the position of the camera.

Since nothing is known about the scene itself, only the relative position of the cameras with respect to each other can be derived. This will thus be performed by first rectifying the respective images, after which step corresponding elements or attributes will be searched for.

The outcome of stages 2 and 3 of FIG. 4b are thus used as scene geometry parameters to define one proper homographic transformation per camera. The transformation is chosen as to mimic a bird's eye's view of the scene. Horizontal planes, which are looked at from an inclined angle in the original image from the camera, are transformed into images as looked from straight above. Since this transformation preserves angular metrics from the real world to the transformed image, this transformation is said to be 'rectifying'.

Note that at the end of stage two each image is transformed in such a way that there exists a similarity between all views. A similarly comprises 4 degrees of freedom: 2 for translation, 1 for rotation and a uniform scaling. These correspond to the panning angle and the three degrees of freedom of the position of the camera. Stage 3 may already have eliminated the panning angle, depending of the accuracy of the similarity measure between the histograms, or the modality in the absolute case.

After having performed the rectification on each image, corresponding features will be searched for. In the embodiment depicted in FIG. 4b a technique called Similarity Invariant Feature Transform (SIFT) is used. This is a known technique searching and describing low-level similar features in images.

This technique is thus applied to search for corresponding features between a reference image, taken from a reference camera, being selected as being one of the cameras of the plurality, and all other images from all other cameras. These features are described according to the SIFT technique. Since many features will be found within horizontal planes, their SIFT description remains invariant between all views, because only a similarity deformation exists. In the case where the panning angle is already accounted for by the third stage, thus when one of the first two paths leading to the priority select step succeeded, the SIFT descriptor may be simplified by eliminating the rotation description. Another option is to use the rotation in the descriptor as an extra constraint on the matching algorithm during the next step. Another RANSAC-like step is used to find a common translation, scaling factor, and (if needed) rotation angle. At this point a second homography matrix (another one than the one mentioned before, which only accounted for rotation) which completely registers a horizontal plane in one view to the same plane in another view is known.

Finally, this second homography matrix for each view can be decomposed into a valid rotation matrix and a translation vector for each camera. Using knowledge about the orientation parameters from stage 2 and 3 eases this decomposition, but is not required.

This calibration can be used on its own, or as input to a refinement method like bundle adjustment, which requires a good initializing estimate.

It can be remarked that in other embodiments the existence of lines in the scene is exploited as well, but several vanishing points e.g. 3 of them, may be looked for. Together they will constitute valid columns of the rotation matrix R. This can be done by a more extended version of the RANSAC and re-estimation steps of stage 2.

After finding a robust estimate of all three vanishing points, which correspond to the three main directions X, Y and Z in the scene, three different homographic transformations are computed per camera. Each mimicking a different side-view (top, front and side). Stage 4 will now match features from each transformed view in one camera to the corresponding features of the reference camera to obtain a good set of correspondences, from which stage 5, again, can compute all calibration data.

An alternative embodiment (not shown in the figures) may search for rectangular objects in a scene. Non-natural scenes often feature windows, tables, doors, computer screens, sheets of paper, all of which are rectangular in shape. Instead of really identifying these objects, which requires more difficult techniques, it is generally sufficient to look for rectangles in the scene in general as these can be considered as corresponding to irregular quadrilaterals in the projected image. The methods for this are similar as for line detection.

A next stage then computes all of the homographic transformations which rectify these irregular quadrilaterals to their original rectangular shapes. Since many other (also non-rectangular) objects are aligned with these rectangular objects (e.g. an object placed on a table, hanging on a wall next to the window, . . . ) they are transformed in the same opportune way, allowing a latter scale invariant feature detecting step to find many of the same features in multiple views. Using the same methods as before in other stages, this again enables a full calibration of all cameras.

Similar embodiments can be thought of, e.g. rectifying ellipses to circles in cases of scenes depicting CD's, cups, round buttons, . . . . Or homographic tranformations which deal with images of scenes with regularly spaced objects, e.g. buttons on a keyboard, wall paper, tiles, curtains, closet doors, . . . . All these instances described here may well be combined as well.

While the principles of the invention have been described above in connection with specific apparatus, it is to be clearly understood that this description is made only by way of example and not as a limitation on the scope of the invention, as defined in the appended claims.

The invention claimed is:

1. A method for determining calibration data for at least two cameras (camera1, camera2) in a multi view position, said method including the steps of:
   determining respective parameters (($h^1_{00}$ ... $h^1_{22}$), ($h^2_{00}$, ... $h^2_{22}$)) for identifying at least one respective homographic transformation on respective images (image1,image2) taken by said cameras of a same scene, by performing respective geometry analyses on said respective images (image1, image2); and
   performing at least one respective homographic transformation on said respective images and a respective feature detection step on respective transformed images thereby obtaining respective sets (feature set1, feature set2) of features on said respective transformed images, such that said calibration data are obtained from matches (m1,..,mk) determined between said respective sets of features.

2. A method according to claim 1 wherein said calibration data comprise information with respect to the relative position between said cameras.

3. A method according to claim 1 wherein said calibration data comprise information with respect to the relative viewing direction differences between said cameras.

4. A method according to claim 1 wherein said at least one respective homographic transformation further comprises an iterative process of pixel coordinates transformation of said respective image, followed by feature detection of the partially transformed image until all pixel coordinates of said respective image (imagel) are transformed.

5. A method according to claim 1 wherein said respective geometry analysis steps comprise determining line segments on said respective images.

6. A method according to claim 1 wherein said respective geometry analysis steps comprise determining curved segments on said respective image.

7. A method according to claim 1 wherein said respective geometry analysis steps comprise performing object recognition on said respective images.

8. A method according to claim 5 wherein said respective line segments are further used for determining a viewpoint angle difference between said at least two cameras.

9. A method according to claim 1 wherein said calibration data are further determined from said respective sets of features.

10. A method according to claim 1 wherein said calibration data are further determined from said parameters for identifying said respective homographic transformations.

11. A method according to claim 1, wherein said calibration data further comprise internal camera parameters which values can be further optimized based on said matches.

12. A device for determining calibration data for at least two cameras (camera1, camera2) in a multi view position, said device adapted to perform the steps of:
   determining respective parameters (($h^1_{00}$ ... $h^1_{22}$), ($h^2_{00}$, ... $h^2_{22}$)) for identifying at least one respective homographic transformation on respective images (image1,image2) taken by said cameras of a same scene, by performing respective geometry analyses on said respective images (image1, image2); and
   performing at least one respective homographic transformation on said respective images and a respective feature detection step on respective transformed images thereby obtaining respective sets (feature set1, feature set2) of features on said respective transformed images, such that said calibration data are obtained from matches (m1,..,mk) determined between said respective sets of features.

13. A computer program product comprising a non-transitory computer usable medium having computer usable program code stored therein, said computer program product when executed performs the following process:
   determining respective parameters (($h^1_{00}$ ... $h^1_{22}$) ($h^2_{00}$, ... $h^2_{22}$)) for identifying at least one respective homographic transformation on respective images (image1,image2) taken by said cameras of a same scene, by performing respective geometry analyses on said respective images (image1, image2); and
   performing at least one respective homographic transformation on said respective images and a respective feature detection step on respective transformed images thereby obtaining respective sets (feature set1, feature set2) of features on said respective transformed images, such that said calibration data are obtained from matches (m1, ... ,mk) determined between said respective sets of features.

14. A device according to claim 12 wherein said calibration data comprise information with respect to the relative position between said cameras.

15. A device according to claim 12 wherein said calibration data comprise information with respect to the relative viewing direction differences between said cameras.

16. A device according to claim 12 wherein said at least one respective homographic transformation further comprises an iterative process of pixel coordinates transformation of said respective image, followed by feature detection of the partially transformed image until all pixel coordinates of said respective image (image1) are transformed.

17. A device according to claim 12 wherein said respective geometry analysis steps comprise determining line segments on said respective images.

18. A device according to claim 12 wherein said respective geometry analysis steps comprise determining curved segments on said respective image.

19. A device according to claim 12 wherein said respective geometry analysis steps comprise performing object recognition on said respective images.

20. A device according to claim 12 wherein said calibration data are further determined from said parameters for identifying said respective homographic transformations.

* * * * *